United States Patent [19]

Abts

[11] 4,214,484
[45] Jul. 29, 1980

[54] ULTRASONIC PARTICULATE SENSING

[75] Inventor: Leigh R. Abts, Providence, R.I.

[73] Assignee: Rhode Island Hospital, Providence, R.I.

[21] Appl. No.: 951,614

[22] Filed: Oct. 16, 1978

[51] Int. Cl.² ............................................. G01N 29/02
[52] U.S. Cl. ...................................... 73/632; 73/642; 73/644
[58] Field of Search ............. 73/642, 632, 644, 194 A; 128/214 E; 340/8 L; 310/335

[56] References Cited

U.S. PATENT DOCUMENTS

| | | |
|---|---|---|
| 3,204,458 | 9/1965 | Gillen . |
| 3,269,172 | 8/1966 | McGaughey . |
| 3,379,051 | 4/1968 | Zeutschel et al. ...................... 73/642 |
| 3,387,604 | 6/1968 | Erikson ................................ 310/335 |
| 3,608,715 | 9/1971 | Snyder . |
| 3,710,615 | 1/1973 | Johnson et al. . |
| 3,774,717 | 11/1973 | Chodorow . |
| 3,816,773 | 6/1974 | Baldwin et al. . |
| 3,821,834 | 7/1974 | McElroy . |
| 3,876,890 | 4/1975 | Brown et al. . |
| 3,906,780 | 9/1975 | Baldwin . |
| 3,974,681 | 8/1976 | Namery . |
| 3,995,179 | 11/1976 | Flournoy et al. ...................... 73/642 |
| 4,011,473 | 3/1977 | Massa . |
| 4,112,773 | 9/1978 | Abts . |

OTHER PUBLICATIONS

McElroy, "Focused Ultrasonic Beams," Automation Industries, Inc., Materials Evaluation Group, Sep., 1966.

Szabo, et al. "Arterial Blood Filter Evaluation by Echo–Ultrasound", *Proc. 27th Annual Conference on Engineering in Medicine and Biology*, 16: 191, 1974.

Patterson, et al. "Microemboli During Cardiopulmonary Bypass Detected by Ultrasound", *Surg., Gyn. and Obs.*, 129: 505–510, 1969.

Martin, et al. "A Simple Way to Eliminate Diffraction Lobes Emitted by Ultrasonic Transducers", *J. Acoust. Soc. Am.* 49, 1668–1669 (1971).

Breazeale, et al. "Reflection of a Gaussian Ultrasonic Beam from a Liquid–Solid Interface", *J. Acoust. Soc. Am.* 56, 866–872 (Sep. 1974).

*Primary Examiner*—Anthony V. Ciarlante

[57] ABSTRACT

A pulse echo device for obtaining information about matter discontinuities in flowing fluid with a transmitter-receiver lens having a concave surface located to direct ultrasonic energy transversely to the direction of fluid flow and to a focal region and a blind hole surrounded by a ridge with an acoustical transducer therein.

14 Claims, 4 Drawing Figures

ULTRASONIC PARTICULATE SENSING

FIELD OF THE INVENTION

This invention relates to obtaining information about matter discontinuities in flowing fluid streams, for example, the size and number of such discontinuities.

BACKGROUND OF THE INVENTION

It is often desirable to be able to measure the size and count the number of particles flowing in a fluid stream. For example, in medicine microembolisms in flowing blood are measured, and in the pharmaceutical industry contaminants in the form of solid particles need to be detected in drug products.

Pulse echo ultrasonic search units are well known, particularly in nondestructive testing systems; bursts or pulses emitted by such units are detected when reflected back from discontinuities. Pulse echo search units have also been used to measure particles in liquid. But these units directed the transmitted signal coaxially longitudinally of the conduit, with a focal point many times the diameter of the conduit in distance from the search unit's transmitting surface. Furthermore, they used flat or convex transmitting surfaces. My recently issued U.S. Pat. No. 4,112,773, hereby incorporated by reference, cites this prior art.

In measuring information using pulse echo search units, it is desirable to avoid generation of spurious returning acoustic signals. One source of these spurious signals is sound waves traveling along other than intended paths between the device and the target. Sensitivity of a unit is limited by pickup of such signals.

SUMMARY OF THE INVENTION

I have discovered that discontinuities in flowing fluids can be detected with greatly improved sensitivity, yet with great simplicity, by, in a first aspect, providing in a pulse echo device a transmitter-receiver lens, the lens having a concave surface positioned to direct ultrasonic energy to a focal region, and a body integral with the lens and positioned on its opposite side for supporting an acoustical transducer, the body including a ridge surrounding and defining a blind hole for mounting the transducer and the blind hole having a bottom surface forming the other surface of the lens, whereby energy directed toward the lens is focused and energy directed toward the ridge is damped. In preferred embodiments, a moat filled with sound absorptive material surrounds the ridge; sound absorptive material covers the transducer in the blind hole; the lens and body are integral with a conduit with a cylindrical interior through which the fluid flows; and the focal region is less than twice the conduit's transverse interior dimension from the concave surface of the lens.

In a second aspect, the invention features providing a sound beam, for focusing by said lens, that has substantially a Gaussian amplitude distribution, i.e., maximum amplitude in the center trailing off to zero amplitude at the edges and without diffraction lobes, by mounting in the blind hole a piezoelectric crystal with a first electrode covering a central portion of the top surface smaller in area than the portion of the bottom surface covered by a second electrode. The ridge and moat damp energy emerging into the plastic around the lens. Sensitivity of the device is thereby greatly increased.

In a third aspect, the invention features providing a non-corrosive liner for the integral conduit-lens-body, adhering the liner at axial locations spaced away from the lens region, and inserting a sound coupling material in the thin annulus between the tube and the lens.

The invention is especially useful in sensing very small particles or other discontinuities (e.g., bubbles in liquid) present in very small quantity. It has advantages of greatly improved sensitivity, high field density, simplicity, resistance to corrosive fluids (e.g., etching fluids), and relative freedom from eddies and other turbulence.

PREFERRED EMBODIMENT

We turn now to the structure and operation of a preferred embodiment, after first briefly describing the drawings.

DRAWINGS

STRUCTURE

Figure 1:
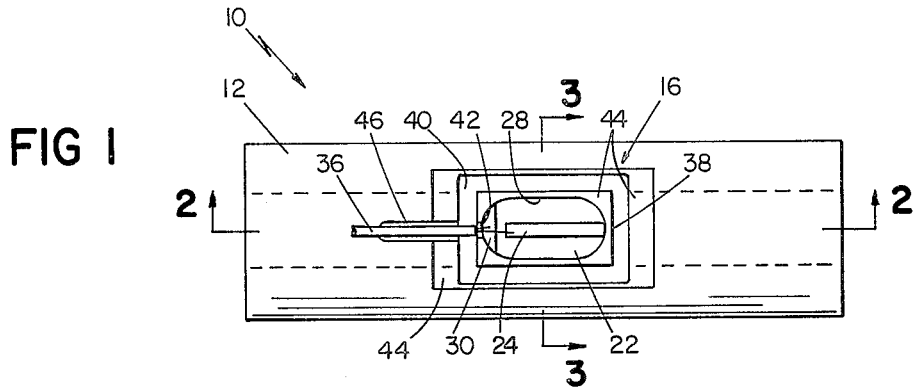
FIG. 1 is a plan view of said embodiment, with the silicone rubber potting removed from the ultrasonic transmitter-receiver.
Figure 2:
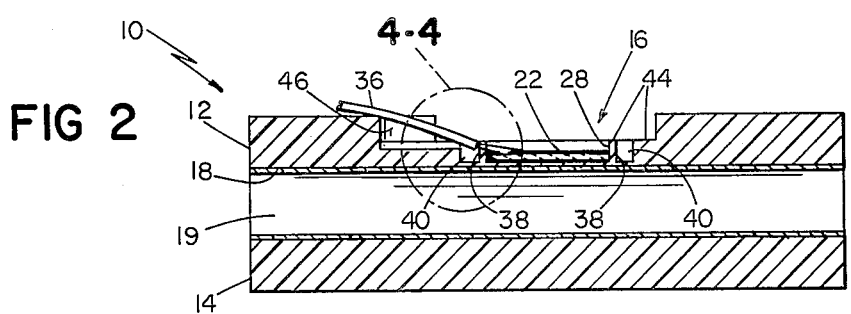
FIG. 2 is a cross sectional view at 2—2 of FIG. 1, also with the silicone rubber removed.

Referring to the figures, there is shown plastic tube 10 (methyl methacrylate) formed of upper and lower semi-annular halves 12, 14 (FIG. 3) held together by epoxy adhesive. Axially midway between ends of tube 10 there is shown ultrasonic transmitter-receiver 16. Interior bore 18 of tube 10 is covered by thin-wall stainless steel (316) tube 19 held in place by epoxy (not shown) applied near the tube ends. Castor oil 20 (FIG. 4) fills the thin annular region between steel tube 19 and bore 18 to provide good acoustic coupling between the steel and plastic. Other coupling materials can be used to fill this annular region as long as they are sound impedance matched with the materials of the tubes. Hose or other couplings (not shown) are provided on the tube ends for connection with a fluid circuit.

Ultrasonic transmitter-receiver 16 includes piezoelectric crystal 22 with upper electrode 24 and lower electrode 26 (both gold) adhered with epoxy in blind hole 28, which has planar sides and semicylindrical ends and extends to within 10 mils of interior bore 18. Crystal 22 (lead metaniobate; 5 megahertz) is 12 mils thick, and has roughly the same plan dimensions as hole 28, fitting closely therein. Upper electrode 24 is 50 mils wide and extends axially down the center of crystal 22. Lower electrode 26 covers the entire lower surface of crystal 22 (being more than twice as wide as upper electrode 24) and a small portion 30 of the upper surface. A 40 mil gap separates electrode portion 30 and upper electrode 24. Wires 32, 34 of lead 36 are soldered to electrodes 24, 26.

Surrounding blind hole 28 are ridge 38, 3/64 inch thick at its thinnest regions, and moat 40. Ridge 38 has groove 42 to facilitate access of lead 36 to crystal 22. Moat 40 is about 3/32 inches wide and of the same depth as blind hole 28 in its transverse portions and even deeper in its longitudinal portions. Coplanar surfaces 44 formed by cutting a flat across tube 10, define the top surface of ridge 38 and extend both transversely and axially of moat 40. Groove 46 breaks surface 44 and extends further toward one end of tube 10 to further facilitate entry of lead 36.

Silicone rubber 50 heavily loaded with 6-micron tungsten powder (FIGS. 3 and 4) fills moat 40, covers crystal 22 in hole 28, and extends into the bottom of groove 46, in all places up to level with surfaces 44, to both aid in damping and to load the crystal to increase band width. The silicone rubber is G.E. RTV-60.

Piezoelectric crystals 24 sold by Valtec Corporation, Hopkinton, MA, are suitable. The crystals are preferably electrically connected to a Matec Pulse Modulator and Receiver Model 6600, the returning signal being put first through Matec Preamplifier Model 251 and then amplified and tuned by a Matec Broad Band Receiver Model 625.

OPERATION

In operation, the crystal may as desired be energized to give a 5 megahertz output for 0.8 microseconds, to transmit through its associated lens an ultrasonic pulse of that duration. Any reflection received may be displayed on an oscilloscope portion of the reflectoscope. The shapes of the curves generated provide information about discontinuities in blood flowing through the passage. Thus number of peaks reflects number of particles and increased amplitude reflects increased particle size, particularly in situations in which only one particle is ordinarily within the field of focus at any given time. The reflectoscope oscilloscope permits visual observation giving useful information.

Moat 40, ridge 38, and silicone rubber 50 all cooperate to dampe acoustic impulses directed horizontally (in the figures) from the edges of crystal 22, thereby allowing undamped transmission of only downwardly directed acoustic energy.

Figure 3:
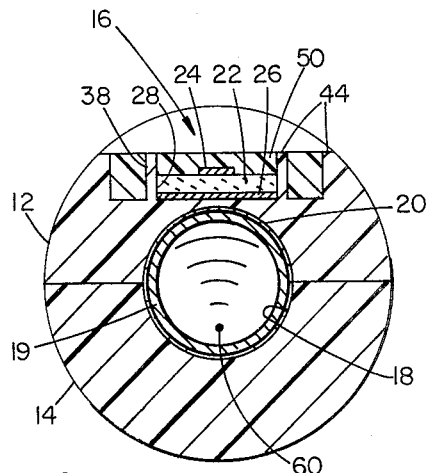
FIG. 3 is an enlarged cross sectional view at 3—3 of FIG. 1, showing the silicone rubber.
Figure 4:
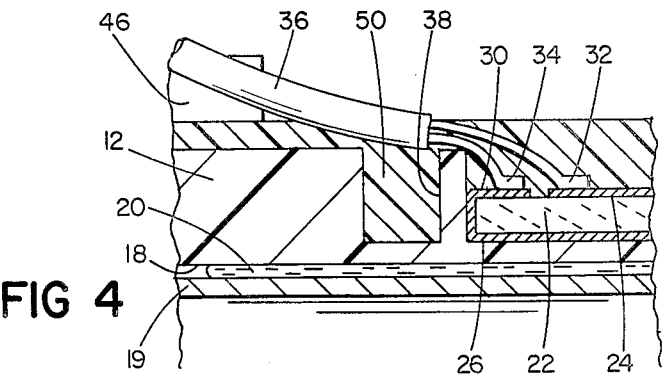
FIG. 4 is an enlarged view of a portion of FIG. 2, showing the silicone rubber, electrodes, and wire leads.

The arrangement of narrow upper electrode 24 and wide lower electrode 26 on either side of crystal 22 produces a sound beam having a near Gaussian shaped amplitude distribution across the transverse dimension of the crystal. No diffraction lobes are generated on either side of the beam. This electrode arrangement about a crystal for producing a Gaussian amplitude distribution is disclosed in articles by Martin and Breazeale, J. Acoust. Soc. Am. 49, 1668–1669 (1971) and by Breazeale and Adler, J. Acoust. Soc. Am. 56, 866–872 (September 1974), both of which are hereby incorporated by reference. The integral lens formed by the concave interior of bore 18 and the flat bottom of hole 28 focuses the Gaussian beam onto focal line 60 (FIG. 3). The absence of diffraction lobes greatly increases the sensitivity of the device to the presence of discontinuities or particulates passing through bore 18.

Stainless steel tube 19 (5 mils thick) inhibits corrosion of bore 18. But because steel is absorptive of the acoustical energy, the wall thickness of tube 19 is kept to a minimum.

OTHER EMBODIMENTS

Other embodiments of the invention will occur to those skilled in the art. For example, the transmitter-receiver could be separate from a conduit; tungsten filled epoxy could substitute for the silicone rubber; Teflon could substitute for stainless steel as a corrosion inhibitor; moat 40 can be eliminated; and plastic tube 10 may be non-transparent and be constructed of other materials.

What is claimed is:

1. A pulse echo device for obtaining information about matter discontinuities in a flowing fluid comprising:
   a transmitter-receiver lens with a concave surface positioned to direct ultrasonic energy transversely to the direction of fluid flow and to a focal region and
   a damping means integral with said lens and positioned on the side opposite said concave surface for supporting an acoustical transducer, said damping means including a ridge spaced apart from a conduit containing the flowing fluid, said ridge surrounding and defining a blind hole, said hole being for receiving said acoustical transducer and having a bottom surface which forms a second surface of said lens opposite said concave surface,
   whereby ultrasonic energy directed toward said lens is focused and energy directed toward said ridge is damped.

2. A pulse echo device for obtaining information about matter discontinuities in a flowing fluid comprising:
   a transmitter-receiver lens with a concave surface positioned to direct ultrasonic energy transversely to the direction of fluid flow and to a focal region and
   an acoustical transducer mounted on a second surface of said lens opposite said concave surface, said transducer including
   a piezoelectric crystal with first and second opposing surfaces,
   a first electrode lying on said first surface and occupying a central portion of said first surface, and
   a second electrode lying on said second opposing surface aligned with said first electrode and occupying at least twice the area occupied by said first electrode,
   whereby energization of said transducer generates a sound beam having a Gaussian-shaped amplitude distribution with peak amplitude in the vicinity of said first electrode and minimum amplitude at the outside edges of said second electrode and
   the sound beam is focused onto a focal region by said lens.

3. The device of claim 2 further comprising:
   a damping means integral with said lens and positioned on the side opposite said concave surface for supporting said acoustical transducer, said damping means including a ridge surrounding and defining a blind hole, said hole being for receiving said acoustical transducer and having a bottom surface which forms said second surface of said lens opposite said concave surface,
   wherein ultrasonic energy directed outward toward said ridge is damped.

4. The device of claim 1 or 3 wherein said body further includes a moat surrounding said ridge.

5. The device of claim 1 or 3 wherein said lens and damping means are both integral with a conduit, said concave surface is integral with the interior surface of said conduit, and said focal region is spaced from said surface in a direction transversely of said conduit of not more than twice the transverse distance across said conduit interior.

6. The device of claim 5 further comprising
   a non-corrosive tube of thickness suitable for adequate sound transmission and of outside diameter closely matching the interior diameter of said conduit, an annular layer of acoustic coupling material between said tube and said conduit interior in the axial region beneath said blind hole, said coupling material being sound impedance matched to said tube and said conduit, means for adhesively securing said tube to said conduit interior at regions axially spaced from said blind hole.

7. The device of claim 1 or 3 wherein said concave surface is cylindrical.

8. The device of claim 1 or 3 wherein said second surface of said lens formed by the bottom of said second blind hole is flat.

9. The device of claim 1 or 3 wherein said blind hole has two planar sides and two opposing semicylindrical sides.

10. The device of claim 4 wherein said moat has rectangular inner cross sections.

11. The device of claim 4 wherein said moat and the region of said blind hole above said transducer is filled with acoustically absorptive material.

12. A pulse echo device comprising:

a conduit, said conduit having a cylindrical interior and including a blind hole and an inwardly concave transmitter-receiver surface, said blind hole being for receiving an acoustical transducer and having a bottom surface which forms a second surface of said lens opposite said concave surface, a non-corrosive tube of thickness suitable for adequate sound transmission and of outside diameter closely matching the interior diameter of said conduit, an annular layer of acoustic coupling material between said tube and said conduit interior in the axial region beneath said blind hole, said coupling material being sound impedance matched to said tube and said conduit, means for axially adhering said tube to said conduit interior, said adhering means positioned at regions axially spaced from said blind hole.

13. The device of claim 12 wherein said non-corrosive tube is stainless steel.

14. The device of claim 13 wherein said non-corrosive tube is a fluorocarbon.

* * * * *